United States Patent [19]
Yoneyoshi et al.

[11] Patent Number: 5,144,039
[45] Date of Patent: Sep. 1, 1992

[54] PROCESS FOR PRODUCING OPTICALLY ACTIVE ALCOHOL

[75] Inventors: Yukio Yoneyoshi, Otsu; Gohfu Suzukamo, Ibaraki; Naoto Konya, Takatsuki; Takaharu Ikeda, Ibaraki, all of Japan

[73] Assignee: Sumitomo Electric Company, Limited, Osaka, Japan

[21] Appl. No.: 471,966

[22] Filed: Jan. 29, 1990

[30] Foreign Application Priority Data

Jan. 30, 1989 [JP] Japan .................. 1-022243
Apr. 18, 1989 [JP] Japan .................. 1-099730

[51] Int. Cl.$^5$ .................. C07D 249/08; C07C 29/143
[52] U.S. Cl. .................. 548/268.4; 568/715; 568/807; 568/808; 568/809; 568/814; 568/880
[58] Field of Search .............. 548/268.4; 568/715, 568/807, 808, 809, 814, 880

[56] References Cited

U.S. PATENT DOCUMENTS 4,760,149  7/1988  Yoneyoshi et al. .............. 548/262
4,923,999  5/1990  Yoneyoshi et al. .............. 548/268.4

FOREIGN PATENT DOCUMENTS 0171175  5/1989  European Pat. Off. .

OTHER PUBLICATIONS

J.C.S. Chem Comm, 1981, 315.
J.C.S. Chem. Comm, 1983, 469.
J. Chem. Soc. Perkin Trans. I, 1673 (1983).
J. Chem. Soc. Perkin Trans. I, 2039 (1985).
J. Chem Soc. Perkin Trans. I, 231 (1981).
Chemical Abstracts, vol. 106, No. 7, Feb. 16, 1987, . . . Abstract No. 50 222b.
Chemical Abstract, vol. 109, No. 13, Sep. 26, 1988, . . . Bianchi et al., Abstract No. 109 922x.
Chemical Abstracts, vol. 105, No. 17, Oct. 27, 1986, . . . Abstract No. 152 607c.
Chemical Abstracts, vol. 103, No. 13, Sep. 30, 1985, . . . Abstract No. 105 273q.
Chemical Abstracts, vol. 101, No. 9, Aug. 27, 1984, . . . Abstract No. 72 353u.
Chemical Abstracts, vol. 98, No. 15, Apr. 11, 1983, . . . Abstract No. 124 796r.
Chemical Abstracts, vol. 97, No. 9, Aug. 30, 1982, . . . Abstract No. 71 600j.
Chemical Abstracts, vol. 95, No. 17, Oct. 26, 1981, . . . Abstract No. 149 766y.
Chemical Abstracts, vol. 95, No. 9, Aug. 31, 1981, . . . Abstract No. 80 386e.

Chemical Abstracts, vol. 93, No. 19, Nov. 10, 1980, . . . Abstract No. 185 896h.

Primary Examiner—Patricia L. Morris
Attorney, Agent, or Firm—Stevens, Davis, Miller & Mosher

[57] ABSTRACT

The process for producing an optically active alcohol of the present invention comprises allowing
(A) an optically active amino alcohol represented by the general formula (I)

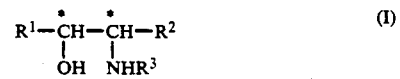

($R^1$ is an aryl group, $R^2$ is a lower alkyl group, $R^3$ is a hydrogen atom or a lower alkyl group, and the carbon atoms having a mark * are each an asymmetric carbon atom) and an acid, or a salt of the optically active amino alcohol (I) and an acid,
(B) a metal borohydride, and
(C) at least one member selected from the group consisting of water, sulfides, cyclic ethers, ethers of mono alcohol to react with
a prochiral ketone represented by the general formula (II)

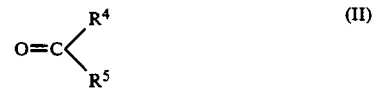

[$R^4$ and $R^5$ are different and each a lower alkyl group, an aryl group, an aralkyl group or a 2-substituted-1-triazoleethylene group represented by the general formula (III)

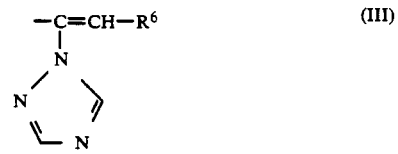

($R^6$ is a halogen- or haloalkyl-substituted or unsubstituted phenyl group or a cycloalkyl group)].

According to the present invention, the optically active alcohol (IV) can be obtained with good efficiency and a high optical purity. Therefore, the present process is advantageous in industrial application, in particular.

33 Claims, No Drawings

PROCESS FOR PRODUCING OPTICALLY ACTIVE ALCOHOL

The present invention relates to a process for producing an optically active alcohol. More particularly, the present invention relates to a process for producing an optically active alcohol by reducing a prochiral ketone with a boron hydride type reducing agent modified with an optically active amino alcohol represented by the general formula (I)

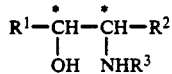
(I)

wherein $R^1$ is an aryl group, $R^2$ is a lower alkyl group, $R^3$ is a hydrogen atom or a lower alkyl group, and the carbon atoms having a mark * are an asymmetric carbon atom.

The present inventors found that the optically active boron hydride type reducing agents obtained by reacting the optically active amino alcohol (I) with an acid and a metal borohydride are useful as an asymmetric reducing agent for ketones to obtain an optically active alcohol. The finding was disclosed in, for example, Japanese Patent Application Kokai (Laid-Open) Nos. 59-184168, 61-68471, 61-18722, 62-10024, U.S. Pat. No. 4,760,149 and EP 0171175 B1.

The present inventors made further study on the process of producing an optically active alcohol by the use of a boron hydride type reducing agent modified with the optically active amino alcohol (I). As a result, it was found that an optically active alcohol can be produced very efficiently by reacting a prochiral ketone compound with (1) a salt between the optically active amino alcohol (I) and an acid, and a metal borohydride in the presence of water, or (2) a reducing agent prepared from the optically active amino alcohol (I), an acid and a metal borohydride, in the presence of a sulfide, a cyclic ether or an ether of mono alcohol. This finding and further investigation led to the completion of the present invention.

According to the present invention, there is provided a process for producing an optically active alcohol comprising allowing (A) an optically active alcohol represented by the general formula (I)

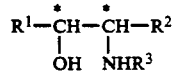
(I)

($R^1$ is an aryl group, $R^2$ is a lower alkyl group, $R^3$ is a hydrogen atom or a lower alkyl group, and the carbon atoms having a mark * are each an asymmetric carbon atom) and an acid, or a salt of the optically active alcohol (I) and an acid, (B) a metal borohydride, and (C) at least one member selected from the group consisting of water, sulfides, cyclic ethers, ethers of mono alcohol to react with a prochiral ketone represented by the general formula (II)

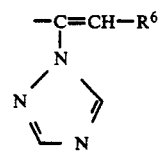
(II)

[$R^4$ and $R^5$ are different and each a lower alkyl group, an aryl group, an aralkyl group or a 2-substituted-1-triazoleethylene group represented by the general formula (III)

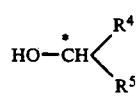
(III)

($R^6$ is a halogen- or haloalkyl-substituted or unsubstituted phenyl group or a cycloalkyl group)].

Another aspect of the present invention relates to a process for producing an optically active alcohol represented by the general formula (IV)

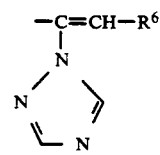
(IV)

[$R^4$ and $R^5$ are different and each a lower alkyl group, an aryl group, an aralkyl group or a 2-substituted-1-triazoleethylene group represented by the general formula (III)

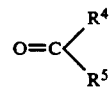
(III)

($R^6$ is a halogen- or haloalkyl-substituted or unsubstituted phenyl group or a cycloalkyl group), and the carbon atom having a mark * is an asymmetric carbon atom], by reducing a ketone compound represented by the general formula (II)

(II)

($R^4$ and $R^5$ have the same definitions as given above) with a boron hydride type reducing agent modified with an optically active amino alcohol represented by the general formula (I)

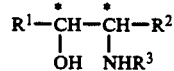
(I)

($R^1$ is an aryl group, $R^2$ is a lower alkyl group, $R^3$ is a hydrogen atom or a lower alkyl group, and the carbon atoms having a mark * are an asymmetric carbon atom), characterized in that the ketone compound (II) is reacted with (1) a salt between the optically active amino alcohol (I) and an acid, and a metal borohydride in the presence of water, or (2) a reducing agent prepared from the optically active amino alcohol (I), an acid and a metal borohydride, in the presence of at least one sulfide, cyclic ether or ether of mono alcohol.

The present invention is described in detail below.

The asymmetric reducing agent used in the present invention is prepared from the optically active amino alcohol (I). As the substituent $R^1$ in the optically active amino alcohol (I), there can be mentioned, for example, a phenyl group which may be substituted with halogen, $C_{1-5}$ alkyl, $C_{1-5}$ alkoxy, cyano, $C_{7-10}$ aralkyloxy, $C_{6-10}$ aryloxy, $C_{1-6}$ alkoxycarbonyl or the like, and a naphthyl group which may be substituted with halogen, $C_{1-5}$ alkyl, cyano, $C_{1-5}$ alkoxy or $C_{1-5}$ alkoxycarbonyl.

Specific examples of $R^1$ are aryl groups such as phenyl, p-tolyl, m-tolyl, o-tolyl, 1-naphthyl, 2,5-dimethylphenyl, 2,5-diethylphenyl, 2,4,6-trimethylphenyl, 2-methoxyphenyl, 2-ethoxyphenyl, 2-propoxyphenyl, 2-isopropoxyphenyl, 2-butoxyphenyl, 2-secbutoxyphenyl, 2-cyclopentyloxyphenyl, 2-cyclohexyloxyphenyl, 2-benzyloxyphenyl, 2-phenoxyphenyl, 2,4-dimethoxyphenyl, 2,4-dipropoxyphenyl, 2,4-dibutoxyphenyl, 2,5-dimethoxyphenyl, 2,5-diethoxyphenyl, 2,5-diisopropoxyphenyl, 2,5-dibutoxyphenyl, 2,4,6-trimethoxyphenyl, 2-methoxy-5-methylphenyl, 2-ethoxy-5-ethylphenyl, 2-methoxy- 5-isopropylphenyl, 2-methoxy-5-tert-butylphenyl, 2-cyanophenyl, 3-cyanophenyl, 4-cyanophenyl, 2-ethoxy-5-methylphenyl, 2-ethoxy-5-ethylphenyl, 2-methoxy-5-isopropylphenyl, 2-ethoxy-5-tertbutylphenyl, 2-propoxy-5-methylphenyl, 2-propoxy-5-ethylphenyl, 2-isopropoxy-5-methylphenyl, 2-isopropoxy-5-isopropylphenyl, 2-isopropyl-5-tert-butylphenyl, 5-chloro-2-methoxyphenyl, 5-chloro-2-ethoxyphenyl, 5-chloro-2-propoxyphenyl, 5-chloro-2-isopropoxyphenyl, 2-methoxycarbonylphenyl, 2-ethoxycarbonylphenyl and the like. Of these, phenyl and 2,5-dimethoxyphenyl are preferred.

The substituent $R^2$ is a lower alkyl group. Preferably it is an alkyl group of 1–4 carbon atoms such as methyl, ethyl, n-propyl, isopropyl, n-butyl, isobutyl, sec-butyl, tert-butyl and the like. As the substituent $R^3$ there can be mentioned, for example, a hydrogen atom and the same lower alkyl groups as mentioned for $R^2$.

Specific examples of the optically active amino alcohol (I) are 2-amino-1-phenyl-1-propanol, 2-amino-1-(2,5-dimethylphenyl)-1-propanol, 2-amino-1-(2-methoxyphenyl)-1-propanol, 2-amino-1-(2,5-dimethoxyphenyl)-1-propanol, 2-amino-1-(2,5-diethoxyphenyl)-1propanol, 2-amino-1-(2-ethoxyphenyl)-1-propanol, 2-amino-1-(2-methoxy-5-methylphenyl)-1-propanol, 2-amino-1-(α-naphthyl)-1-propanol, 2-amino-1-(2-phenoxyphenyl)-1-propanol, 2-amino-1-(2-isopropoxyphenyl)-1-propanol, 2-amino-1-(2-propoxyphenyl)-1-propanol, 2-amino-1-(2-benzyloxyphenyl)-1-propanol, 2-amino-1-(2,4-dimethoxyphenyl)-1-propanol, phenyl)-1-propanol, 2-amino-1-(5-chloro-2-methoxyphenyl)-1-propanol, 2-amino-1-(2,5-dipropoxyphenyl)-1-propanol, ephedrine etc.

As the acid, there can be mentioned, for example, mineral acids such as hydrochloric acid, sulfuric acid, nitric acid, phosphoric acid and the like; carboxylic acids such as acetic acid and the like; and organic sulfonic acids such as p-toluenesulfonic acid and the like.

As the salt of the optically active amino alcohol (I) and an acid, there can be mentioned, for example, salts of the optically active amino alcohol (I) and one of the above acids. In the present process, the salt may be used as such, or may be formed from the optically active amino alcohol (I) and an acid in the system and successively used.

As the metal borohydride, there can be mentioned, for example, sodium borohydride, potassium borohydride lithium borohydride and zinc borohydride. Sodium borohydride is ordinarily used because of its high availability.

As the substituents $R^4$ and $R^5$ in the ketone compound represented by the general formula (II), there can be mentioned, for example, aryl groups having 5-17 total carbon atoms such as phenyl, 2-, 3- and 4-pyridyl, halogen-substituted phenyl (e.g. o-, m- and p-chlorophenyls, o-, m-, p-bromophenyls, o-, m- and p-fluorophenyls, 2,3-, 2,4-, 2,5- and 2,6-dichlorophenyls), phenyl substituted with $C_{1-6}$ alkyl (e.g. o-, m- and p-methylphenyls, o-, m- and p-ethylphenyls, o-, m- and p-butylphenyls, 2,3-, 2,4-, 2,5- and 2,6-dimethylphenyls), phenyl substituted with $C_{1-6}$ alkoxy (e.g. o-, m- and p-methoxyphenyls, o-, m- and p-ethoxyphenyls, o-, m- and p-propoxyphenyls), benzyloxy-substituted phenyl (e.g. o-, m- and p-benzyloxyphenyls, 2-benzyloxy-3-methylphenyl, 2-benzyloxy-4-methylphenyl, 2-benzyloxy-5-methylphenyl, 2-benzyloxy-5-tert-butylphenyl, 2-benzyloxy-3-methoxyphenyl, 2-benzyloxy-4-methoxyphenyl, 2-benzyloxy-5-methoxyphenyl, 2-benzyloxy-3,5-dichlorophenyl), α-naphthyl, β-naphthyl, $C_{1-6}$ lower alkyl groups (e.g. methyl, ethyl, propyl, butyl, pentyl, cyclopentyl, hexyl, cyclohexyl, chloromethyl, bromomethyl, fluoromethyl, iodomethyl, 1-chloroethyl, 2-chloroethyl, 1-bromoethyl, 2-bromoethyl, 1-fluoroethyl, 1-chloropropyl, 3-chloropropyl, 1-bromopropyl, 4-bromopropyl, 1-bromo-1-methylethyl), and $C_{7-11}$ aralkyl groups (e.g. benzyl, o-, m- and p-tolylmethyls, (o-, m- or p-ethylphenyl)methyl, (2,3-, 2,4-, 2,5- or 2,6-dimethylphenyl)methyl, 2-phenylethyl, 2-(o-, m- or p-tolyl)ethyl, (2,3-, 2,4-, 2,5- or 2,6-dimethylphenyl)ethyl, 3-phenylpropyl, (α-naphthyl)methyl, (β-naphthyl)methyl]. As the substituent $R^6$, there can be mentioned, for example, 2-substituted-1-triazoleethylene groups having, as the 2-substituent, phenyl, chlorophenyl, bromophenyl, dichlorophenyl, dibromophenyl, trifluoromethylphenyl, trichloromethylphenyl, tribromomethylphenyl, cyclohexyl or the like.

As typical examples of the ketone compound (II), there can be mentioned acetophenone, 2-chloroacetophenone, 2'-chloroacetophenone, 3'-chloroacetophenone, 4'-chloroacetophenone, propiophenone, 3-chloropropiophenone, butyrophenone, 4-chlorobutyrophenone, 2-bromoisobutyrophenone, isobutyrophenone, α-acetonaphthone, β-acetonaphthone, phenyl benzyl ketone, phenyl p-tolylmethyl ketone, phenyl m-tolylmethyl ketone, phenyl o-tolylmethyl ketone, 2-butanone, 2-pentanone, 2-hexanone, 3-hexanone, 2-heptanone, 2-octanone, 1-phenyl-2-(1,2,4-triazol-1-yl)-4,4-dimethyl1-penten-3-one, 1-(4-chlorophenyl)-2-(1,2,4-triazol-1-yl)-4,4-dimethyl-1-penten-3-one, 1-(2,4-dichlorophenyl)-2-(1,2,4-triazol-1-yl)-4,4-dimethyl-1-penten-3-one, 1-cyclohexyl-2-(1,2,4-triazol-1-yl)-4,4-dimethyl-1-penten-3-one, (1-(4-trifluoromethylphenyl)-2-(1,2,4-triazol-1-yl) yl)-4,4-dimethyl-1-penten-3-one, 1-(3-bromophenyl)-2(1,2,4-triazol-1-yl)-4,4-dimethyl-1-3-one and 1-(4-fluorophenyl)-2-(1,2,4-triazol-1-yl)-4,4-dimethyl-1-penten-3-one.

Then, there is explained a method wherein the salt between the optically active amino alcohol (I) and the acid and the metal borohydride are reacted with the ketone compound (II) in the presence of water.

The reaction is effected ordinarily in the presence of a solvent. The solvent can be any unless it takes part in the reaction. There can be mentioned, for example, aromatic hydrocarbons such as benzene, toluene, xylene, chlorobenzene and the like; halogenated hydrocarbons such as methylene chloride, 1,2-dichloroethane, chloroform, carbon tetrachloride and the like; ethers such as diethyl ether, tetrahydrofuran, diglyme, dioxane and the like; and their mixtures. The solvent is used in an amount of ordinarily 1–50 parts by weight per part by weight of the ketone compound (II).

It is possible that an alcohol be used in combination with the above solvent. The use of a secondary or tertiary alcohol, in particular, together with the solvent is preferable because it brings about advantages such as improved optical yield and the like. As the secondary alcohol, there can be mentioned, for example, isopropanol, sec-butanol, cyclopentanol, cyclohexanol, menthol, methylpropyl alcohol, methylisobutyl alcohol and 2-octanol. As the tertiary alcohol, there can be mentioned, for example, tertbutanol, tert-amyl alcohol, 1,1,2,2-tetramethylpropanol, 1,1,2-trimethylpropanol, 2,2,3-tri- methyl-3-pentanol, 2,2,3,4-tetramethyl-3-pentanol, 2,2,3,4,4-pentamethyl-3-pentanol, 3-methyl-3-pentanol, 3-methyl- 3-hexanol, 1-ethyl-1-ethylpropanol, 1,1-diethylpropanol, 1,1dimethylbutanol, 2,3-dimethyl-3-pentanol and 2,3,4-trimethyl-3-pentanol. The secondary or tertiary alcohol is used in an amount of ordinarily at least 0.5 mole, preferably 1–30 moles, more preferably 3–15 moles per mole of the optically active amino alcohol (I).

When the component (C) is water, the reaction is ordinarily effected by adding water to a mixture consisting of a solvent, the metal borohydride, the acid of the optically active amino alcohol (I) and the salt, and the ketone compound (II). The reaction can also be effected by adding an aqueous solution of the metal borohydride to a mixture consisting of a solvent, the salt of the optically active amino alcohol (I) and the acid, and the ketone compound (II).

The salt of the optically active amino alcohol (I) and the acid is used in an amount of ordinarily at least 0.2 mole, preferably 0.2–5 moles, more preferably 0.3–1 mole per mole of the ketone compound (II).

The metal borohydride is used in an amount of ordinarily at least 0.5 mole, preferably 0.5–2 moles, more preferably 0.8–1.5 moles (in terms of boron) per ml of the ketone compound (II), and in an amount of ordinarily 1.25–5 moles, preferably 1.4–3.5 moles (in terms of boron) per mole of the optically active amino alcohol (I).

Water is used in an amount of ordinarily 1–20 moles per mole of the optically active amino alcohol (I).

The reaction temperature is in a range of ordinarily 0°–100° C., preferably 0°–50° C. The reaction is effected ordinarily in an inert gas atmosphere such as nitrogen, argon or the like.

After the reaction has been effected as above, the reaction mixture is ordinarily mixed with an aqueous solution of a mineral acid such as hydrochloric acid, sulfuric acid or the like to separate the organic layer from the aqueous layer. The organic layer is washed with water and dried. The resulting organic layer is subjected to distillation to remove the organic solvent to easily obtain an intended optically active alcohol (IV).

The optical yield can be known by measuring the optical rotation of the product obtained, or by directly measuring the enantiomer ratio of the product by high-performance liquid chromatography with optically active packing materials.

The optically active amino alcohol (I) can be easily recovered with the steric configuration kept unchanged, by adding an aqueous alkali solution to the above separated aqueous layer and then extracting the resulting mixture with an organic solvent, and can be reused.

There can thus be obtained an intended optically active alcohol (IV). In the present invention, a very short reaction time can be used; the preparation of the reducing agent and the reduction reaction can be effected simultaneously in the same container; the amount of the optically active amino alcohol (I) as a ligand can be low; therefore, the present process is advantageous in industrial application, in particular.

Next, there is explained a case wherein the component (C) is a sulfide, a cyclic ether or an ether of mono alcohol, i.e. a method wherein a reducing agent prepared from the optically active amino alcohol (I), the acid and the metal borohydride is reacted with the ketone compound (II) in the presence of a sulfide, a cyclic ether or an ether of mono alcohol.

As the sulfide, there can be mentioned, for example, monosulfides such as dimethyl sulfide, diethyl sulfide, dipropyl sulfide, diisopropyl sulfide, dibutyl sulfide, di-sec-butyl sulfide, di-tert-butyl sulfide, dipentyl sulfide, dihexyl sulfide, dicyclohexyl sulfide, didodecyl sulfide, distearyl sulfide and the like; thiophenes such as tetrahydrothiophene, thiophene and the like; and disulfides such as dimethyl disulfide, diethyl disulfide, dipropyl disulfide, diisopropyl disulfide, dibutyl disulfide, di-sec-butyl disulfide, di-tert-butyl disulfide, dipentyl disulfide, dihexyl disulfide, dicyclohexyl disulfide, didodecyl disulfide, distearyl disulfide and the like.

As the cyclic ether, there can be mentioned, for example, furans such as tetrahydrofuran and the like; dioxanes such as dioxane, 1,3-dioxane and the like; pyrans such as tetrahydropyran and the like; and crown ethers such as 12-crown-4 and the like. As the ether of mono alcohol, there can be mentioned, for example, methyl ether, diethyl ether, dipropyl ether, diisopropyl ether and dibutyl ether.

The sulfide, the cyclic ether or the ether of mono alcohol is used in an amount of ordinarily at least 0.2 mole, preferably 0.5–20 moles per mole of the optically active amino alcohol (I).

The preparation of the reducing agent is ordinarily effected in an inert gas atmosphere such as nitrogen, argon or the like, using a solvent. The solvent is not particularly restricted unless it takes part in the reaction. There can be mentioned, for example, aromatic hydrocarbons (e.g. benzene, toluene, xylene, chlorobenzene), halogenated hydrocarbons (e.g. methylene chloride, 1,2-dichloroethane, chloroform, carbon tetrachloride), ethers (e.g. diglyme, triglyme) and their mixtures.

In reacting the optically active amino alcohol (I) with the acid and the metal borohydride, ordinarily the optically active amino alcohol (I) is firstly reacted with the acid and then reacted with the metal borohydride. In this case, it is possible that a salt of the optically active amino alcohol (I) and the acid be used as a starting material and reacted with the metal borohydride. Ordinarily, a mixture of the salt, a solvent and the sulfide, cyclic ether or ether of mono alcohol is treated with a solution of the metal borohydride dissolved in a solvent such as diglyme, triglyme, dimethylformamide, 1,3-dimethyl-2-imidazolidinone or the like.

It is also possible that a mixture of the optically active amino alcohol (I), the metal borohydride, a solvent and the sulfide, cyclic ether or ether of primary alcohol be directly reacted with the acid.

The acid is used ordinarily in an equivalent amount to that of the optically active amino alcohol (I). The metal borohydride is used in an amount of ordinarily 0.7-1.3 moles, preferably 1 mole (in terms of boron) per mole of the optically active amino alcohol (I).

The reaction temperature has no particular restriction but is ordinarily −78° to +100° C., preferably −40° to +100° C.

Thus there is obtained an optically active boron hydride type reducing agent. The reducing agent may be used after being isolated, but is ordinarily used in the form of the reaction mixture per se. The reducing agent has a very high activity and can reduce, in a small amount, a prochiral ketone compound efficiently to form an optically active alcohol at a high optical yield.

In reducing the ketone compound (II), the reducing agent can be used in an amount of ordinarily at least 0.5 mole, preferably 0.5-2 moles, more preferably 0.7-1.5 moles [in terms of the optically active amino alcohol (I)] per mole of the ketone compound The reduction reaction is effected ordinarily in the presence of a solvent. The solvent has no particular restriction unless it takes part in the reaction. There can be mentioned, for example, aromatic hydrocarbons (e.g. benzene, toluene, xylene, chlorobenzene), halogenated hydrocarbons (e.g. methylene chloride, 1,2-dichloroethane, chloroform, carbon tetrachloride), ethers (e.g. diethyl ether, tetrahydrofuran, dioxane, diglyme) and their mixtures The solvent is used in an amount of ordinarily 1-50 parts by weight per part by weight of the ketone compound.

The reduction reaction is effected ordinarily in the same inert gas atmosphere as mentioned above. The reaction temperature is ordinarily −78° to +100° C., preferably −40° to +50° C.

After the reduction reaction, the reaction mixture is ordinarily mixed with an aqueous solution of a mineral acid such as hydrochloric acid, sulfuric acid or the like to separate the organic layer from the aqueous layer. The organic layer is washed with water, dried and subjected to distillation to remove the solvent to easily obtain an intended optically active alcohol (IV).

The progress of the reaction can be followed by means of gas chromatography, liquid chromatography or the like. The optical yield can be known by measuring the optical rotation of the product obtained, or by directly measuring the enantiomer ratio of the product by means of high-performance liquid chromatography with optically active packing materials.

The optically active amino alcohol (I) can be easily recovered with the steric configuration kept unchanged, by adding an alkali to the above separated aqueous layer and then extracting the resulting mixture with an organic solvent, and can be reused.

There can thus be obtained an intended optically active alcohol (IV). In the present invention, the optically active alcohol (IV) can be obtained with good efficiency and at a high optical purity. Therefore, the present process is advantageous in industrial application, in particular.

The present invention is described in more detail below by way of Examples. However, the present invention is in no way restricted to these Examples.

EXAMPLE 1

0.244 Gram (1.3 mmoles) of (+)-norephedrine hydrochloride was suspended in 1.4 ml of monochlorobenzene in a nitrogen atmosphere. Thereto was added 0.162 g (2.6 mmoles) of dimethyl sulfide. The mixture was cooled to −20° C.

Then, there was added a solution of 0.0492 g (1.3 mmoles) of sodium borohydride dissolved in 1.1 ml of triglyme. The mixture was returned from −20° C. to room temperature in 2 hours. To the suspension was added a solution of 0.60 g (1.85 mmoles) of (E)-1-(2,4-dichlorophenyl)-2-(1,2,4-triazol-1-yl)-4,4-dimethyl-1-penten-3-one dissolved in 2.25 ml of monochlorobenzene. The mixture was stirred for 90 hours at room temperature.

Then, 5 ml of 10% hydrochloric acid was added. The organic layer was washed with water and concentrated under reduced pressure to obtain 0.61 g of crude crystals of (-)-(E)-(2,4-dichlorophenyl)-2-(1,2,4-triazol-1-yl)-4,4-dimethyl-1-penten-3-ol.

The product was analyzed by gas chromatography, which indicated a conversion of 97.4% and a composition consisting of 96.9% of an E-form alcohol and 3.1% of a Z-form alcohol. There existed substantially no saturated-form alcohol wherein both of the carbonyl group and the carbon-to-carbon double bond had been reduced, and substantially no saturated-form ketone wherein only the carbon-to-carbon double bond had been reduced.

Analysis by high-performance liquid chromatography indicated that the enantiomer ratio of the E-form alcohol was 82% of a (−)-isomer and 18% of a (+)-isomer.

TABLE 1

|  | Component (C) | Reaction time (hr) | Conversion (%) | Product E/Z/S*1 (%) | (+)/(−)*2 |
| --- | --- | --- | --- | --- | --- |
| Example |  |  |  |  |  |
| 1 | Dimethyl sulfide | 90 | 97.4 | 96.9/3.1/— | 18/82 |
| 2 | Tetrahydrothiophene | 91 | 92.2 | 96.1/3.4/0.5 | 19/81 |
| 3 | Diethyl sulfide | 28 | 94.3 | 97.3/2.6/0.1 | 19/81 |
| 4 | Di-tert-butyl disulfide | 45 | 74.0 | 92.4/6.4/1.2 | 16/84 |
| 5 | Tetrahydrofuran | 45 | 76.3 | 93.1/6.8/0.1 | 16/84 |
| 6 | Thiophene | 19 | 71.8 | 92.1/6.1/1.8 | 15/85 |
| 7 | Dimethyl sulfide | 91 | 95.0 | 96.4/3.2/0.4 | 18/82 |
| Comparative Example 1 | — | 91 | 67.2 | 86.9/5.6/7.5 | 16/84 |

*1E refers to an E-form alcohol; Z refers to a Z-form alcohol; and S refers to a saturated-form alcohol and a saturated-form ketone.
*2Enantiomer ratio of an E-form alcohol

EXAMPLES 2-6

Optically active alcohols were produced in the same manner as in Example 1 except that dimethyl sulfide was replaced by tetrahydrothiophene, diethyl sulfide, di-tert-butyl disulfide, tetrahydrofuran or thiophene and that there was used a reaction time as shown in Table 1. The results are shown in Table 1.

EXAMPLE 7

An optically active alcohol was produced in the same manner as in Example 1 except that monochlorobenzene was replaced by 1,2-dichloroethane and the reaction time was changed to 91 hours. The results are shown in Table 1.

COMPARATIVE EXAMPLE 1

An optically active alcohol was produced in the same manner as in Example 1 except that there was used no dimethyl sulfide and the reaction temperature was changed to 91 hours. The results are shown in Table 1.

EXAMPLE 8

The same procedure as in Example 1 was repeated except that dimethyl sulfide was used in an amount of 0.081 g (1.3 mmoles), (E)-1-(2,4-dichlorophenyl)-2-(1,2,4-triazol-1-yl)-4,4-dimethyl-1-penten-3-one was replaced by 0.484 g (1.85 mmoles) of (E)-1-cyclohexyl-2-(1,2,4-triazol-1-yl)-4,4-dimethyl-1-penten-3-one, and the reduction reaction was effected for 24 hours, to obtain 0.489 g of crude (+)-(E)-1-cyclohexyl-2-(1,2,4-triazol-1-yl)-4,4-dimethyl-1-penten-3-ol.

The conversion was 96.9% and the product had a composition consisting of 89.6% of an E-form alcohol, 9.8% of a Z-form alcohol and 0.6% of a saturated-form alcohol. The enantiomer ratio of the E-form alcohol was 24.9% of a (−)-isomer and 75.1% of a (+)-isomer.

EXAMPLE 9

The same procedure as in Example 1 was repeated except that (+)-norephedrine hydrochloride was -) replaced by 0.322 g (1.3 mmoles) of (+)-1-(2,5-dimethoxyphenyl)-2-amino-1-propanol hydrochloride and triglyme was replaced by 0.4 ml of dimethylformamide, to obtain 0.61 g of crude crystals of (−)-(E)-(2,4-dichlorophenyl)-2-(1,2,4-triazol-1-yl)-4,4-dimethyl-1-penten-3-ol. The results are shown in Table 2.

COMPARATIVE EXAMPLE 2

An optically active alcohol was obtained in the same manner as in Example 9 except that no dimethyl sulfide was used. The results are shown in Table 2.

EXAMPLE 10

An optically active alcohol was produced in the same manner as in Example 1 except that dimethyl sulfide was used in an amount of 0.81 g (1.3 mmoles), (+)-norephedrine hydrochloride was replaced by 0.322 g (1.3 mmoles) of (+)-1-(2,5-dimethoxyphenyl)-2-amino-1-propanol hydrochloride, (E)-1-(2,4-dichlorophenyl)-2(1,2,4-triazol-1-yl)-4,4-dimethyl-1-penten-3-one was replaced by 0.536 g (1.85 mmoles) of (E)-1-(4-chlorophenyl)-2-(1,2,4-triazol-1-yl)-4,4-dimethyl-1-penten-3-one, and the reduction reaction was conducted for 24 hours. The results are shown in Table 2.

COMPARATIVE EXAMPLE 3

An optically active alcohol was produced in the same manner as in Example 10 except that no dimethyl sulfide was used. The results are shown in Table 2.

TABLE 2

| | Reaction time (hr) | Conversion (%) | Product E/Z/S*[1] (%) | (+)/(−)*[2] |
|---|---|---|---|---|
| Example | | | | |
| 9 | 28 | 99.6 | 97.9/2.0/0.1 | 10/90 |
| 10 | 24 | 93.5 | 88.5/9.6/1.9 | 10/90 |
| Comparative Example | | | | |
| 2 | 28 | 80.5 | 83.8/7.9/8.3 | 6/94 |
| 3 | 24 | 61.7 | 88.2/6.9/4.9 | 8/92 |

*[1] E refers to an E-form alcohol; Z refers to a Z-form alcohol; and S refers to a saturated-form alcohol and a saturated-form ketone.
*[2] Enantiomer ratio of an E-form alcohol

EXAMPLE 11

The same procedure as in Example 1 was repeated except that (+)-norephedrine hydrochloride was replaced by (−)-norephedrine hydrochloride, triglyme was replaced by 0.4 ml of dimethylformamide, dimethyl sulfide was replaced by diethyl sulfide, monochlorobenzene was replaced by 1,2-dichloroethane, (E)-1-(2,4-dichlorophenyl)-2-(1,2,4-triazol-1-yl)-4,4-dimethyl-1-penten-3-one was replaced by 0.27 g (1.85 mmoles) of phenyl isopropyl ketone, and the reduction reaction was conducted for 18.5 hours, to obtain 0.27 g of crude (−)-phenylisobutyl alcohol.

The conversion was 97.3%. The enantiomer ratio of the product was 36% of a (+)-isomer and 64% of a (−)-isomer.

COMPARATIVE EXAMPLE 4

An optically active alcohol was produced in the same manner as in Example 11 except that no diethyl sulfide was used.

The conversion was 88.7%. The enantiomer ratio of the product was 32% of a (+)-isomer and 68% of a (−)-isomer.

EXAMPLE 12

0.657 g (3.5 mmoles) of (+)-norephedrine hydrochloride was suspended in 4.1 g (61.3 mmoles) of tetrahydrofuran in a nitrogen atmosphere. The suspension was cooled to −30° C.

Thereto was added a solution of 0.1324 g (3.5 mmoles) of sodium borohydride dissolved in 0.8 ml of dimethylformamide. The mixture was returned from −30° C. to room temperature in 2 hours. To the suspension was added a solution of 1.62 g (5.0 mmoles) of (E)-1-(2,4-dichlorophenyl)-2-(1,2,4-triazol-1-yl)-4,4-dimethyl-1-penten-3-one dissolved in 5.06 g of monochlorobenzene. The mixture was stirred for 19 hours at room temperature. Then, the work up and analyses were conducted in the same manner as in Example 1.

The conversion was 90.5%. The product had a composition consisting of 94.9% of an E-form alcohol and 5.1% of a Z-form alcohol. There existed substantially no saturated-form alcohol wherein both of the carbonyl group and the carbon-to-carbon double bond had been reduced, and substantially no saturated-form ketone wherein only the carbon-to-carbon double bond had been reduced.

The enantiomer ratio of the E-form alcohol was 80% of a (−)-isomer and 20% of a (+)-isomer.

EXAMPLE 13

A reducing agent was prepared in the same manner as in Example 12. It was concentrated under reduced pressure to remove about the total volume of tetrahydrofuran used and about the half volume of dimethylformamide used. The resulting concentrate was mixed with 3.3 g of chlorobenzene.

Thereto was added a solution of 1.62 g (5.0 mmoles) of (E)-1-(2,4-dichlorophenyl)-2-(1,2,4-triazol-1-yl)-4,4-dimethyl-1-penten-3-one dissolved in 5.06 g of monochlorobenzene. The mixture was stirred for 15 hours at room temperature. Then, the work up and analyses were conducted in the same manner as in Example 12. The results are shown in Table 3.

EXAMPLE 14

An optically active alcohol was produced in the same manner as in Example 13 except that tetrahydrofuran was replaced by dioxane. The results are shown in Table 3.

EXAMPLE 15

An optically active alcohol was produced in the same manner as in Example 13 except that (+)-norephedrine hydrochloride was replaced by 0.867 g (3.5 mmoles) of (+)-1-(2,5-dimethoxyphenyl)-2-amino-1propanol hydrochloride. The results are shown in Table 3.

EXAMPLE 16

In a nitrogen atmosphere, 0.1324 g (3.5 mmoles) of sodium borohydride was suspended in a solution of 0.53 g (3.5 mmoles) of (+)-norephedrine dissolved in 3.5 g (49 mmoles) of tetrahydrofuran Thereto was added, at room temperature in 1 hour, a solution of 97% sulfuric acid (0.182 g, 1.8 mmoles) dissolved in 0.88 g (12.3 mmoles) of tetrahydrofuran. The mixture was concentrated under reduced pressure to remove almost all the tetrahydrofuran used.

Then, 1.96 g of monochlorobenzene was added. Further, there was added a solution of 1.62 g (5.0 mmoles) of (E)-1-(2,4-dichlorophenyl)-2-(1,2,4-triazol-1-yl)-4,4-dimethyl-1-penten-3-one dissolved in 2.42 g of monochlorobenzene. The mixture was stirred for 15 hours at 25° C. Then, the work up and analyses were conducted in the same manner as in Example 1. The results are shown in Table 3.

EXAMPLE 17

An optically active alcohol was produced in the same manner as in Example 16 except that (+)-norephedrine and sulfuric acid were replaced by 0.7 g (3.5 mmoles) of (+)-norephedrine sulfate and that a mixture consisting of said sulfate, 4.4 g (61 mmoles) of tetrahydrofuran and 0.1324 g (3.5 mmoles) of sodium borohydride was stirred for 6 hours and then concentrated under reduced pressure. The results are shown in Table 3.

EXAMPLE 18

An optically active alcohol was produced in the same manner as in Example 13 except that tetrahydrofuran was replaced by 3.6 g of diethyl ether. The results are shown in Table 3.

TABLE 3

| | Reaction time (hr) | Conversion (%) | Product E/Z/S*[1] (%) | (+)/(−)*[2] |
|---|---|---|---|---|
| Example | | | | |
| 12 | 19 | 90.5 | 94.1/5.1/— | 20/80 |
| 13 | 15 | 98.1 | 98.7/1.2/0.1 | 16/84 |
| 14 | 15 | 92.5 | 97.2/2.8/— | 16/84 |
| 15 | 15 | 98.3 | 98.9/0.9/0.2 | 8/92 |
| 16 | 15 | 99.0 | 99.0/0.8/0.2 | 14/86 |
| 17 | 15 | 98.7 | 96.3/1.5/2.2 | 17/83 |
| 18 | 19 | 80.3 | 92.2/7.6/0.2 | 16/84 |
| Comparative Example | | | | |
| 5 | 19 | 64.1 | 89.8/9.9/0.3 | 16/84 |
| 6 | 15 | 65.5 | 90.1/9.7/0.2 | 15/85 |

*[1]E refers to an E-form alcohol; Z refers to a Z-form alcohol; and S refers to a saturated-form alcohol and a saturated-form ketone.
*[2]Enantiomer ratio of an E-form alcohol

COMPARATIVE EXAMPLE 5

An optically active alcohol wa produced in the same manner as in Example 12 except that tetrahydrofuran was replaced by monochlorobenzene. The results are shown in Table 3.

COMPARATIVE EXAMPLE 6

An optically active alcohol was produced in the same manner as in Example 13 except that tetrahydrofuran was replaced by monochlorobenzene. The results are shown in Table 3.

EXAMPLE 19

0.488 g (2.6 mmoles) of (+)-norephedrine hydrochloride was suspended in 3 ml of monochlorobenzene in a nitrogen atmosphere. Thereto was added 0.323 g (5.2 mmoles) of methyl sulfide. The mixture was cooled to −20° C.

Thereto was added a solution of 0.0984 g (2.6 mmoles) of sodium borohydride dissolved in 1 ml of $d_7$-dimethylformamide. The mixture was returned from −20° C. to room temperature in 2 hours. Thereto was added 1 ml of deuterated chloroform, and the mixture was measured for $^{11}B$ NMR spectrum, which was shown below in percent by area (standard: $BF_3.OEt_2$).

−19.4 ppm (85.7%), −110.0 ppm (1.2%), −7.4 ppm (0.5%), 7.8 ppm (12.5%).

EXAMPLE 20

In a nitrogen atmosphere, 1.495 g (9.9 mmoles) of (+)-norephedrine was dissolved in a mixed solvent consisting of 5.61 g of monochlorobenzene and 3.57 g of tetrahydrofuran. Therein was suspended 0.347 g (9.9 mmoles) of sodium borohydride. Then, 0.514 g (5.1 mmoles) of 97% sulfuric acid was added in 1 hour. The mixture was stirred for 1.5 hours. The mixture was then measured for $11_B$ NMR spectrum in the same manner as in Example 19.

−20.4 ppm (92.9%), 1.7 ppm (0.5%), 5.2 ppm (1.3%), 13.2 ppm (2.4%), 19.0 ppm (2.9%),

EXAMPLE 21

In a nitrogen atmosphere, 2.384 g (12.7 mmoles) of (+)-norephedrine hydrochloride and 0.9612 g (25.41 mmoles) of sodium borohydride were suspended in a solution consisting of 7.49 g (23.1 mmoles) of (E)-1-(2,4-dichlorophenyl)-2-(1,2,4-triazol-1-yl)-4,4-dimethyl-1-penten-3-one (E/Z=99.7/0.3), 22.5 g of monochlorobenzene and 14.6 g of tert-butanol.

The mixture was cooled to 15° C. Thereto was added by drops 2.0 g (111.1 mmoles) of water in 3.25 hours with stirring at the same temperature. Thereafter, the mixture was stirred for 1 hour at 25° C.

20 Milliliters of 10% hydrochloric acid was added. The mixture was stirred for 1 hour at 50° C. The organic layer was separated, washed with 10% hydrochloric acid and water in this order. The resultant mixture was dried and subjected to evaporation of the solvent to obtain 7.50 g of a product. The product was analyzed by gas chromatography. It consisted of 97.7 % of (E)-1-(2,4-dichlorophenyl)-2(1,2,4-triazol-1-yl)-4,4-dimethyl-1-penten-3-ol [E-form alcohol], 2.1% of (Z)-1-(2,4-dichlorophenyl)-2-(1,2,4-triazol-1-yl)-4, 4-dimethyl-1-penten-3-ol [Z-form alcohol] and 0.2% of 1-(2,4-dichlorophenyl)-2-(1,2,4-triazol-1-yl)-4,4-dimethylpentan-3-ol [saturated-form alcohol]. The conversion was 99.8%.

The enantiomer ratio of the E-form alcohol was analyzed by high-performance liquid chromatography using an optically active column. The enantiomer ratio was 86% of a (−)-isomer and 14% of a (+)-isomer.

EXAMPLES 22–32

Optically active alcohols were produced in the same manner as in Example 21 except that there were used the solvents shown in Table 4. The results are shown in Table 4.

EXAMPLE 33

An optically active alcohol was produced in the same manner as in Example 23 except that water was used in an amount of 1.25 g (69.4 mmoles) and the temperature and stirring time after water addition were 15° C. and 3 hours, respectively.

The conversion was 99.9%. The product composition was 97.5% of an E-form alcohol, 2.3% of a Z-form alcohol and 0.2% of a saturated-form alcohol The enantiomer ratio of the E-form alcohol was 82.5% of (−)-isomer and 17.5% of (+)-isomer.

EXAMPLE 34

An optically active alcohol was produced in the same manner as in Example 21 except that 35.2 g of monochlorobenzene and 1.3 g (6.93 mmoles) of (+)-norephedrine hydrochloride were used and that water was added at 10° C. in 1.75 hours and then stirring was effected for 3.5 hours at 25° C.

The conversion was 99.9%. The product consisted of 98.3% of an E-form alcohol, 0.8% of a Z-form alcohol and 0.9% of a saturated-form alcohol. The enantiomer ratio of the E-form alcohol was 77.4% of a (−)-isomer and 22.6% of a (+)-isomer.

EXAMPLE 35

An optically active alcohol was produced in the same manner as in Example 21 except that norephedrine hydrochloride was replaced by (−)-2-amino-1-(2,5-dimethoxyphenyl)-1-propanol hydrochloride. The results are shown in Table 5.

EXAMPLE 36

An optically active alcohol was produced in the same manner as in Example 21 except that norephedrine hydrochloride was replaced by (+)-2-amino-1-(2,5-dimethylphenyl)-1-propanol hydrochloride. The results are shown in Table 5.

EXAMPLE 37

An optically active alcohol was produced in the same manner as in Example 21 except that norephedrine hydrochloride was replaced by (−)-ephedrine hydrochloride. The results are shown in Table 5.

TABLE 5

| Example No. | Conversion (%) | Product | | | (−)/(+) ratio of E-form alcohol |
|---|---|---|---|---|---|
| | | E-form alcohols | Z-form alcohols | Saturated-form alcohol | |
| 35 | 99.9 | 98.0 | 1.8 | 0.2 | 18/82 |
| 36 | 99.9 | 97.6 | 2.0 | 0.4 | 85/15 |
| 37 | 70.0 | 97.4 | 2.4 | 0.2 | 27/73 |

EXAMPLE 38

5.61 Grams of crystals were obtained in the same manner as in Example 21 except that (E)-1-(2,4-dichlorophenyl)-2-(1,2,4-triazol-1-yl)-4,4-dimethyl-1-penten-3-one was replaced by 5.66 g (19.53 mmoles) of (E)-1-(4-chlorophenyl)-2-(1,2,4-triazol-1-yl)-4,4-

TABLE 4

| Example No. | Solvent(s) | (g) | Conversion (%) | Product | | | (−)/(+) ratio of E-form alcohol |
|---|---|---|---|---|---|---|---|
| | | | | E-form alcohols | Z-form alcohols | Saturated-form alcohol | |
| 22 | Monochlorobenzene | (22.5) | 99.8 | 97.8 | 2.0 | 0.2 | 86/14 |
| | tert-Amyl alcohol | (17.3) | | | | | |
| 23 | Monochlorobenzene | (22.5) | 97.5 | 97.3 | 2.2 | 0.5 | 81/19 |
| | sec-Butanol | (14.6) | | | | | |
| 24 | Monochlorobenzene | (22.5) | 93.4 | 97.7 | 2.1 | 0.2 | 68/32 |
| | n-Butanol | (14.6) | | | | | |
| 25 | Monochlorobenzene | (22.5) | 95.6 | 97.2 | 2.3 | 0.5 | 76/24 |
| | Cyclohexanol | (19.7) | | | | | |
| 26 | Monochlorobenzene | (22.5) | 95.7 | 97.7 | 2.1 | 0.2 | 81/19 |
| | 2-Octanol | (25.6) | | | | | |
| 27 | Monochlorobenzene | (22.5) | 98.6 | 97.7 | 1.9 | 0.4 | 78/22 |
| | Isopropanol | (9.8) | | | | | |
| 28 | Monochlorobenzene | (22.5) | 93.1 | 96.1 | 3.5 | 0.4 | 72/28 |
| 29 | Diethyl ether | (22.5) | 99.1 | 94.8 | 4.5 | 0.7 | 80/20 |
| | tert-butanol | (14.6) | | | | | |
| 30 | Chloroform | (22.5) | 99.7 | 97.3 | 2.0 | 0.7 | 86/14 |
| | tert-Butanol | (14.6) | | | | | |
| 31 | Toluene | (22.5) | 98.8 | 97.7 | 2.0 | 0.3 | 86/14 |
| | tert-Butanol | (14.6) | | | | | |
| 32 | 1,2-Dichloroethane | (22.5) | 98.3 | 96.7 | 2.9 | 0.4 | 86/14 |
| | tert-Butanol | (14.6) | | | | | | dimethyl-1-penten-3-one (E/Z=97/3), 18.7 g of monochlorobenzene and 17.5 g of tert-butanol were used, and water was added by drops at 10° C. and the subsequent stirring was effected for 2 hours. The conversion was 94%. The product consisted of 93.3% of (E)-1-(4-chlorophenyl)-2-(1,2,4-triazol-1-yl)-4,4-dimethyl-1-penten-3-ol (E-form alcohol), 5.6% of (Z)-1-(4-chlorophenyl)-2-(1,2,4-triazol-1-yl)-4,4-dimethyl-1-penten-3-ol (Z-form alcohol) and 1.1% of 1-(4-chlorophenyl)-2-(1,2,4-triazol-1-yl)-4,4-dimethylpentan-3-ol (saturated-form alcohol). The enantiomer ratio of the E-form alcohol was 83.5% of a (−)-isomer and 16.5% of a (+)-isomer.

EXAMPLE 39

An optically active alcohol was produced in the same manner as in Example 21 except that (E)-1-(2,4-dichlorophenyl)-2-(1,2,4-triazol-1-yl)-4,4-dimethyl-1-penten-3-one was replaced by (E)-1-cyclohexyl-2-(1,2,4-triazol-1-yl)-4,4-dimethyl-1-penten-3-one (E/Z=99.9/0.1) and water addition was made in 1 hour.

The conversion was 100%. The product consisted of 95.2% of (E)-1-cyclohexyl-2-(1,2,4-triazol-1-yl)-4,4-dimethyl-1-penten-3-ol (E-form alcohol), 4.3% of (Z)-1-cyclohexyl-2-(1,2,4-triazol-1-yl)-4,4-dimethyl-1-penten-3-ol (Z-form alcohol) and 0.5% of 1-cyclohexyl-2-(1,2,4-triazol-1-yl)-4,4-dimethylpentan-3-ol (saturated-form alcohol). The enantiomer ratio of the E-form alcohol was 14% of a (−)-isomer and 86% of a (+)-isomer.

EXAMPLE 40

An optically active alcohol was produced in the same manner as in Example 21 except that (+)-norephedrine hydrochloride was replaced by (−)-norephedrine hydrochloride, and the procedure of suspending (+)-norephedrine hydrochloride together with sodium borohydride and adding water thereto by drops was replaced by suspending (−)-norephedrine hydrochloride only and adding dropwise a solution consisting of 0.961 g of sodium borohydride, 2.0 g of water and 7 mg of sodium hydroxide thereto in 2 hours.

The conversion was 99.5%. The product consisted of 93.3% of an E-form alcohol, 6.4% of a Z-form alcohol and 0.3% of a saturated-form alcohol. The enantiomer ratio of the E-form alcohol was 84% of a (+)-isomer and 16% of a (−)-isomer.

EXAMPLE 41

In a nitrogen atmosphere, 0.834 g (4.44 mmoles) of (−)-norephedrine hydrochloride and 0.3363 g (8.89 mmoles) of sodium borohydride were suspended in a solution consisting of 1.1 g (7.42 mmoles) of phenyl isopropyl ketone, 25.1 g of 1,2-dichloroethane and 4.39 g of tert-butanol.

The mixture was cooled to 25° C. To the mixture being stirred at the same temperature was dropwise added 0.6 g (33.3 mmoles) of water in 1 hour. The resulting mixture was stirred for 2 hours at 25° C. Then, the subsequent work up and analyses were conducted in the same manner as in Example 21.

The conversion was 94.3%. The enantiomer ratio was 69.6% of a (−)-isomer and 30.4% of a (+)-isomer.

COMPARATIVE EXAMPLE 7

In a nitrogen atmosphere, 6.49 g of (+)-norephedrine hydrochloride was suspended in 96 ml of 1,2-dichloroethane. The suspension was cooled to −25° C. Thereto was added a solution of 1.31 g of sodium borohydride dissolved in 19 ml of dimethylformamide. The suspension was returned from −25° C. to 25° C. in 2 hours. To the suspension being stirred at the same temperature was added a solution of 7.49 g of the same (E)-1-(2,4-dichlorophenyl)-2-(1,2,4-triazol-1-yl)-4,4-dimethyl-1-penten-3-one as used in Example 21, dissolved in 78 ml of 1,2-dichloroethane. The mixture was stirred for a total of 25 hours. (During the stirring, sampling of small amount was made after 1, 3 and 6 hours.) Then, the post-treatment and analyses were conducted in the same manner as in Example 21. The conversion was 97%. The product consisted of 98.1% of an E-form alcohol, 1.7% of a Z-form alcohol and 0.2% of a saturated-form alcohol. The enantiomer ratio of the E-form alcohol was 85% of a (−)-isomer and 15% of a (+)-isomer. Incidentally, the conversions after 1, 3 and 6 hours were 23%, 52% and 77%, respectively.

COMPARATIVE EXAMPLE 8

2.384 g of (+)-norephedrine hydrochloride was suspended in 13.7 g of monochlorobenzene in a nitrogen atmosphere. The suspension was cooled to −25° C. Thereto were added a solution consisting of 0.961 g of sodium borohydride and 10 ml of dimethylformamide. The mixture was returned to 25° C. in 2 hours.

To the mixture being stirred at 15° C. was added a solution consisting of 7.48 g of the same (E)-1-(2,4-dichlorophenyl)-2-(1,2,4-triazol-1-yl)-4,4-dimethyl-1-penten-3-one as used in Example 21 and 16.4 g of monochlorobenzene. The resulting mixture was stirred for 4 hours at the same temperature. Then, the work up and analyses were made in the same manner as in Example 21.

The conversion was 98.2%. The product consisted of 63.9% of an E-form alcohol, 25.2% of a Z-form alcohol and 38.7% of a saturated alcohol. The enantiomer ratio of the E-form alcohol was 70.3% of a (−)-isomer and 29.7% of a (+)-isomer.

What is claimed is:

1. A process for producing an optically active alcohol comprising:
   1) reacting
      (A) an optically active amino alcohol represented by the formula (I)

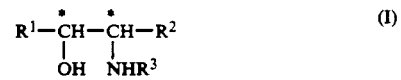

$$R^1-\overset{*}{\underset{OH}{C}}H-\overset{*}{\underset{NHR^3}{C}}H-R^2 \qquad (I)$$

wherein
   $R^1$ is phenyl which may be substituted by $C_1$–$C_5$ alkyl or $C_1$–$C_5$ alkoxy, $R^2$ is $C_1$–$C_4$ alkyl, $R^3$ is hydrogen, and the carbon atoms having a mark * are each an asymmetric carbon atom, and
   an acid selected from the group consisting of mineral acids, carboxylic acids and organic sulfonic acids, or an acceptable salt of the optically active amino alcohol (I) and said acid, with
   (B) a metal borohydride, in the presence of
   (C) at least one member selected from the group consisting of water, sulfides selected from the group consisting of dialkyl monosulfides in which each alkyl has 1–4 carbon atoms, dialkyl disulfides in which each alkyl has 1–4 carbon atoms and cyclic sulfides having 4 carbon atoms, cyclic ethers having 4 carbon atoms and dialkyl ethers in which each alkyl has 1–4 carbon atoms, to obtain a product and 2) reacting the product of step 1 with a prochiral ketone represented by the formula (II)

wherein $R^4$ and $R^5$ are different and selected from the group consisting of $C_1$–$C_6$ alkyl, aryl having 5–17 carbon atoms, aralkyl having 7–11 carbon atoms and 2-substituted-1-triazoleethylene represented by the formula (III)

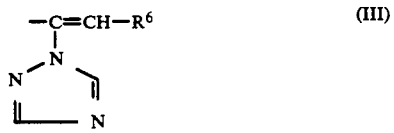

wherein $R^6$ is a halogen- or haloalkyl-substituted or unsubstituted phenyl or cycloalkyl.

2. A process according to claim 1, wherein the acid is selected from the group consisting of hydrochloric acid, sulfuric acid, nitric acid, phosphoric acid, acetic acid, benzenesulfonic acid and p-toluenesulfonic acid.

3. A process according to claim 1, wherein the substituents $R^4$ and $R^5$ in the formula (II) are each an aryl group having 6–17 total carbon atoms, a lower alkyl group of 1–6 total carbon atoms or an aralkyl group of 7–11 total carbon atoms.

4. A process according to claim 1, wherein the substituents $R^4$ and $R^5$ are each a 2-substituted-1-triazoleethylene group represented by the formula (III).

5. A process according to claim 4, wherein the substituent $R^6$ in the formula (III) is selected from the group consisting of phenyl, chlorophenyl, bromophenyl, dichlorophenyl, dibromophenyl, trifluorophenyl, trichloromethylphenyl, tribromomethylphenyl and cyclohexyl.

6. A process according to claim 1, wherein the component (C) is water and the component (A) is a salt of the optically active amino alcohol (I) and an acid as defined in claim 1.

7. A process according to claim 6, wherein the salt of the optically active amino alcohol (I) and an acid is used in an amount of 0.3–1 mole per mole of the ketone compound (II).

8. A process according to claim 6, wherein the metal borohydride is used in an amount of 0.8–1.5 moles (in terms of boron) per mole of the ketone compound (II).

9. A process according to claim 6, wherein the metal borohydride is used in an amount of 1.4–3.5 moles (in terms of boron) per mole of the optically active amino alcohol (I).

10. A process according to claim 6, which is carried out in the presence of a secondary or tertiary alcohol having 2–10 carbon atoms.

11. A process according to claim 10, wherein the secondary or tertiary alcohol having 2–10 carbon atoms is used in an amount of 3–15 moles per mole of the optically active amino alcohol (I).

12. A process according to claim 6, wherein the solvent is selected from the group consisting of an aromatic hydrocarbon, a halogenated hydrocarbon or an ether.

13. A process according to claim 12, wherein the solvent is used in an amount of 1–50 parts by weight per part by weight of the ketone compound (II).

14. A process according to claim 6, which further comprises adding water to a mixture consisting of a solvent, the metal borohydride, the salt of the optically active amino alcohol (I) and an acid, and the ketone compound (II).

15. A process according to claim 6, wherein water is used in an amount of 1–20 moles per mole of the optically active amino alcohol (I).

16. A process according to claim 6, wherein the reaction temperature is 0°–50° C.

17. A process according to claim 1, wherein the component (C) is a sulfide as defined in claim 1, a cyclic ether as defined in claim 1 or a dialkyl ether as defined in claim 1, the component (A) is the optically active amino alcohol and an acid, and a reducing agent prepared from the component (A) and the component (B) is reacted with the ketone (II).

18. A process according to claim 17, wherein the component (C) is a sulfide.

19. A process according to claim 18, wherein the sulfide is a monosulfide, a thiophene or a disulfide.

20. A process according to claim 17, wherein the component (C) is a cyclic ether.

21. A process according to claim 20, wherein the cyclic ether is selected from the group consisting of tetrahydrofuran, a dioxane, and a pyran.

22. A process according to claim 17, wherein the component (C) is a dialkyl ether.

23. A process according to claim 22, wherein the dialkyl ether has 2–8 total carbon atoms.

24. A process according to claim 17, wherein the sulfide, cyclic ether or dialkyl ether is used in an amount of 0.5–20 moles per mole of the optically active amino alcohol (I).

25. A process according to claim 17, wherein the product of step 1) is prepared using an aromatic hydrocarbon,, a halogenated hydrocarbon or an ether as a solvent.

26. A process according to claim 17, wherein the component (A) is the optically active amino alcohol (I) and an acid, the component (C) is a sulfide, a cyclic ether or a dialkyl ether, and the reducing agent is prepared by reacting a mixture of the component (A), the component (C) and a solvent with the component (B).

27. A process according to claim 17, wherein the metal borohydride is used in an amount of 0.7–1.3 moles (in terms of boron) per mole of the optically active amino alcohol (I).

28. A process according to claim 17, wherein the reducing agent is prepared at a temperature of −40° to +100° C.

29. A process according to claim 17, wherein the reducing agent is used in an amount of 0.5–2 moles per mole of the ketone compound (II).

30. A process according to claim 17, wherein at least one solvent selected from the group consisting of aromatic hydrocarbons, halogenated hydrocarbons and ethers is used in step 2) as a solvent.

31. A process according to claim 30, wherein the solvent is used in an amount of 1–50 parts by weight per part by weight of the ketone (II).

32. A process according to claim 17, wherein the reduction reaction is carried out at a temperature of −40° to +50° C.

33. A process for producing an optically active alcohol represented by the formula (IV)

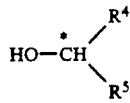

(IV)

wherein $R^4$ and $R^5$ are different and selected from the group consisting of $C_1$-$C_6$ alkyl, aryl having 5-17 carbon atoms, aralkyl having 7-11 carbon atoms and 2-substituted-1-triazoleethylene represented by the formula (III)

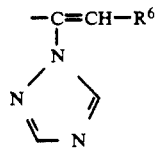

(III)

in which $R^6$ is halogen- or haloalkyl-substituted or unsubstituted phenyl or cycloalkyl, and the carbon atom having a mark * is an asymmetric carbon atom, by reducing a ketone compound represented by the formula (II)

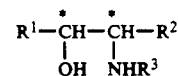

(II)

wherein $R^4$ and $R^5$ are as defined above, with a boron hydride type reducing agent modified with an optically active amino alcohol represented by the formula (I)

$$R^1-\underset{OH}{\overset{*}{C}H}-\underset{NHR^3}{\overset{*}{C}H}-R^2 \quad (I)$$

in which $R^1$ is phenyl which may be substituted by $C_1$-$C_5$ alkyl or $C_1$-$C_5$ alkoxy, $R^2$ is $C_1$-$C_4$ alkyl, $R^3$ is hydrogen, and the carbon atoms having a mark * are asymmetric carbon atoms, characterized in that the ketone compound (II) is reacted with (1) an acceptable salt of the optically active amino alcohol (I) and an acid selected from the group consisting of mineral acids, carboxylic acids and organic sulfonic acids, and a metal borohydride in the presence of water, or (2) a reducing agent prepared from the optically active amino alcohol (I), said acid and a metal borohydride, in the presence of at least one sulfide selected from the group consisting of dialkyl monosulfides in which each alkyl has 1-4 carbon atoms, dialkyl disulfides in which each alkyl has 1-4 carbon atoms and cyclic sulfides having 4 carbon atoms, cyclic ether having a 4 carbon atoms or dialkyl ether in which each alkyl has 1-4 carbon atoms.

* * * * *

UNITED STATES PATENT AND TRADEMARK OFFICE
CERTIFICATE OF CORRECTION

PATENT NO. : 5,144,039
DATED : September 1, 1992
INVENTOR(S) : Yukio YONEYOSHI et al It is certified that error appears in the above-identified patent and that said Letters Patent is hereby corrected as shown below:

On the title page , please correct the designation of the assignee to read:

-- [73] Assignee: SUMITOMO CHEMICAL COMPANY, LIMITED, Osaka, Japan. --

Signed and Sealed this

First Day of March, 1994

Attest:

BRUCE LEHMAN

Attesting Officer

Commissioner of Patents and Trademarks